(12) United States Patent
Felix et al.

(10) Patent No.: US 8,626,277 B2
(45) Date of Patent: Jan. 7, 2014

(54) COMPUTER-IMPLEMENTED ELECTROCARDIOGRAPHIC DATA PROCESSOR WITH TIME STAMP CORRELATION

(75) Inventors: Jason Felix, Vashon Island, WA (US); Gust H. Bardy, Carnation, WA (US)

(73) Assignee: Cardiac Science Corporation, Waukesha, WI (US)

( * ) Notice: Subject to any disclaimer, the term of this patent is extended or adjusted under 35 U.S.C. 154(b) by 0 days.

(21) Appl. No.: 13/568,099

(22) Filed: Aug. 6, 2012

(65) Prior Publication Data

US 2012/0302906 A1 Nov. 29, 2012

Related U.S. Application Data

(63) Continuation of application No. 12/901,460, filed on Oct. 8, 2010, now Pat. No. 8,239,012.

(51) Int. Cl.
*A61B 5/04* (2006.01)
*A61N 1/00* (2006.01)

(52) U.S. Cl.
USPC ............... 600/513; 600/5; 607/31; 607/59

(58) Field of Classification Search
USPC ................... 607/31, 59; 600/5, 513
See application file for complete search history.

(56) References Cited

U.S. PATENT DOCUMENTS

| | | | |
|---|---|---|---|
| 3,215,136 | A | 11/1965 | Holter et al. |
| 4,123,785 | A | 10/1978 | Cherry et al. |
| 4,532,934 | A | 8/1985 | Kelen |
| 4,550,502 | A | 11/1985 | Grayzel |
| 4,716,903 | A | 1/1988 | Hansen et al. |
| 4,809,705 | A | 3/1989 | Ascher |
| 4,915,656 | A | 4/1990 | Alferness |
| 5,168,876 | A | 12/1992 | Quedens et al. |
| 5,215,098 | A | 6/1993 | Steinhaus |
| D341,423 | S | 11/1993 | Bible |

(Continued)

FOREIGN PATENT DOCUMENTS

| | | |
|---|---|---|
| DE | 19955211 | 5/2001 |
| WO | WO03/032192 | 4/2003 |

(Continued)

OTHER PUBLICATIONS

P. Libby et al., "Braunwald's Heart Disease—A Textbook of Cardiovascular Medicine," Chs. 11, pp. 125-148 and 12, pp. 149-193 (8th ed. 2008), American Heart Association.

(Continued)

*Primary Examiner* — Nicole F Lavert
(74) *Attorney, Agent, or Firm* — Patterson Thuente Pedersen, P.A.

(57) ABSTRACT

A computer-implemented electrocardiographic data processor with time stamp correlation is provided. A monitoring circuit includes a persistent memory and power supply that powers an encoder that determines a differential voltage between a current discrete digital voltage value and a prior voltage value. The differential voltage is stored into the persistent memory in a digitized data stream representative of analog cardiac action potential signals. Digitally-encoded voltage values and time stamps are retrieved from the persistent memory. A post-processing application executes. A set of output voltages and voltage differences that each correspond to lower and upper bounds of voltage is stored. Each retrieved voltage value is compared to the voltage bounds and the voltage differences within which each retrieved voltage value falls is identified. The output voltages corresponding to the voltage differences is selected. A display depicts the output voltages as reproduced analog cardiac action potential signals and correlates the time stamps.

3 Claims, 2 Drawing Sheets

(56) References Cited

U.S. PATENT DOCUMENTS

| | | |
|---|---|---|
| 5,392,784 A | 2/1995 | Gudaitis |
| D357,069 S | 4/1995 | Plahn et al. |
| 5,402,780 A | 4/1995 | Faasse, Jr. |
| 5,402,884 A | 4/1995 | Gilman et al. |
| 5,458,141 A | 10/1995 | Neil |
| 5,473,537 A | 12/1995 | Glazer et al. |
| 5,579,919 A | 12/1996 | Gilman et al. |
| 5,582,181 A | 12/1996 | Ruess |
| D377,983 S | 2/1997 | Sabri et al. |
| 5,623,935 A | 4/1997 | Faisandier |
| 5,697,955 A | 12/1997 | Stolte |
| 5,749,902 A | 5/1998 | Olson et al. |
| 5,817,151 A | 10/1998 | Olson et al. |
| 5,850,920 A | 12/1998 | Gilman et al. |
| D407,159 S | 3/1999 | Roberg |
| 5,906,583 A | 5/1999 | Rogel |
| 5,951,598 A | 9/1999 | Bishay et al. |
| 5,984,102 A | 11/1999 | Tay |
| 6,101,413 A | 8/2000 | Olson et al. |
| 6,115,638 A | 9/2000 | Groenke |
| 6,117,077 A | 9/2000 | Del Mar et al. |
| 6,134,479 A | 10/2000 | Brewer et al. |
| 6,148,233 A | 11/2000 | Owen et al. |
| 6,269,267 B1 | 7/2001 | Bardy et al. |
| 6,272,385 B1 | 8/2001 | Bishay et al. |
| 6,301,502 B1 | 10/2001 | Owen et al. |
| 6,304,773 B1 | 10/2001 | Taylor et al. |
| 6,304,780 B1 | 10/2001 | Owen et al. |
| 6,304,783 B1 | 10/2001 | Lyster et al. |
| 6,374,138 B1 | 4/2002 | Owen et al. |
| 6,418,342 B1 | 7/2002 | Owen et al. |
| 6,427,083 B1 | 7/2002 | Owen et al. |
| 6,456,872 B1 | 9/2002 | Faisandier |
| 6,546,285 B1 | 4/2003 | Owen et al. |
| 6,605,046 B1 | 8/2003 | Del Mar |
| 6,607,485 B2 | 8/2003 | Bardy |
| 6,671,545 B2 | 12/2003 | Fincke |
| 6,671,547 B2 | 12/2003 | Lyster et al. |
| 6,694,186 B2 | 2/2004 | Bardy |
| 6,704,595 B2 | 3/2004 | Bardy |
| 6,705,991 B2 | 3/2004 | Bardy |
| 6,754,523 B2 | 6/2004 | Toole |
| 6,782,293 B2 | 8/2004 | Dupelle et al. |
| 6,860,897 B2 | 3/2005 | Bardy |
| 6,866,629 B2 | 3/2005 | Bardy |
| 6,887,201 B2 | 5/2005 | Bardy |
| 6,893,397 B2 | 5/2005 | Bardy |
| 6,904,312 B2 | 6/2005 | Bardy |
| 6,908,431 B2 | 6/2005 | Bardy |
| 6,913,577 B2 | 7/2005 | Bardy |
| 6,944,498 B2 | 9/2005 | Owen et al. |
| 6,960,167 B2 | 11/2005 | Bardy |
| 6,978,169 B1 | 12/2005 | Guerra |
| 6,993,377 B2 | 1/2006 | Flick et al. |
| 7,027,864 B2 | 4/2006 | Snyder et al. |
| 7,065,401 B2 | 6/2006 | Worden |
| 7,085,601 B1 | 8/2006 | Bardy et al. |
| 7,104,955 B2 | 9/2006 | Bardy |
| 7,134,996 B2 | 11/2006 | Bardy |
| 7,147,600 B2 | 12/2006 | Bardy |
| 7,215,991 B2 | 5/2007 | Besson et al. |
| 7,248,916 B2 | 7/2007 | Bardy |
| 7,257,438 B2 | 8/2007 | Kinast |
| D558,882 S | 1/2008 | Brady |
| 7,328,061 B2 | 2/2008 | Rowlandson et al. |
| 7,412,395 B2 | 8/2008 | Rowlandson et al. |
| D606,656 S | 12/2009 | Kobayashi et al. |
| 7,756,721 B1 | 7/2010 | Falchuk et al. |
| 7,787,943 B2 | 8/2010 | McDonough |
| 7,874,993 B2 | 1/2011 | Bardy |
| 7,881,785 B2 | 2/2011 | Nassif et al. |
| D639,437 S | 6/2011 | Bishay et al. |
| 7,959,574 B2 | 6/2011 | Bardy |
| 8,231,539 B2 | 7/2012 | Bardy |
| 8,231,540 B2 | 7/2012 | Bardy |
| 8,239,012 B2 | 8/2012 | Felix et al. |
| 8,260,414 B2 | 9/2012 | Nassif et al. |
| 8,266,008 B1 | 9/2012 | Siegel et al. |
| 8,277,378 B2 | 10/2012 | Bardy |
| 8,285,370 B2 | 10/2012 | Felix et al. |
| 8,308,650 B2 | 11/2012 | Bardy |
| 8,366,629 B2 | 2/2013 | Bardy |
| 2002/0120310 A1 | 8/2002 | Linden et al. |
| 2002/0193668 A1 | 12/2002 | Munneke |
| 2003/0004547 A1 | 1/2003 | Owen et al. |
| 2003/0073916 A1 | 4/2003 | Yonce |
| 2003/0083559 A1 | 5/2003 | Thompson |
| 2003/0139785 A1 | 7/2003 | Riff et al. |
| 2004/0008123 A1 | 1/2004 | Carrender et al. |
| 2004/0019288 A1 | 1/2004 | Kinast |
| 2004/0034284 A1 | 2/2004 | Aversano et al. |
| 2004/0049132 A1 | 3/2004 | Barron et al. |
| 2004/0087836 A1 | 5/2004 | Green et al. |
| 2004/0148194 A1 | 7/2004 | Wellons et al. |
| 2004/0243435 A1 | 12/2004 | Williams |
| 2004/0256453 A1 | 12/2004 | Lammle |
| 2004/0260188 A1 | 12/2004 | Syed et al. |
| 2005/0096717 A1 | 5/2005 | Bishay et al. |
| 2005/0108055 A1 | 5/2005 | Ott et al. |
| 2005/0154267 A1 | 7/2005 | Bardy |
| 2005/0182308 A1 | 8/2005 | Bardy |
| 2005/0182309 A1 | 8/2005 | Bardy |
| 2005/0228243 A1 | 10/2005 | Bardy |
| 2005/0245839 A1 | 11/2005 | Stivoric et al. |
| 2006/0025824 A1 | 2/2006 | Freeman et al. |
| 2006/0041201 A1 | 2/2006 | Behbehani et al. |
| 2006/0122469 A1 | 6/2006 | Martel |
| 2006/0224072 A1 | 10/2006 | Shennib |
| 2006/0235320 A1 | 10/2006 | Tan et al. |
| 2006/0253006 A1 | 11/2006 | Bardy |
| 2007/0003115 A1 | 1/2007 | Patton et al. |
| 2007/0050209 A1 | 3/2007 | Yered |
| 2007/0078324 A1 | 4/2007 | Wijisiriwardana |
| 2007/0093719 A1 | 4/2007 | Nichols, Jr. et al. |
| 2007/0100667 A1 | 5/2007 | Bardy |
| 2007/0123801 A1 | 5/2007 | Goldberger et al. |
| 2007/0136091 A1 | 6/2007 | McTaggart |
| 2007/0179357 A1 | 8/2007 | Bardy |
| 2007/0203415 A1 | 8/2007 | Bardy |
| 2007/0203423 A1 | 8/2007 | Bardy |
| 2007/0225611 A1 | 9/2007 | Kumar et al. |
| 2007/0244405 A1 | 10/2007 | Xue et al. |
| 2007/0249946 A1 | 10/2007 | Kumar et al. |
| 2007/0255153 A1 | 11/2007 | Kumar et al. |
| 2007/0265510 A1 | 11/2007 | Bardy |
| 2007/0276270 A1 | 11/2007 | Tran |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2008/0051668 A1 | 2/2008 | Bardy |
| 2008/0058661 A1 | 3/2008 | Bardy |
| 2008/0139953 A1 | 6/2008 | Baker et al. |
| 2008/0194927 A1 | 8/2008 | KenKnight et al. |
| 2008/0208014 A1 | 8/2008 | KenKnight et al. |
| 2008/0284599 A1 | 11/2008 | Zdeblick et al. |
| 2008/0288026 A1 | 11/2008 | Cross et al. |
| 2008/0306359 A1 | 12/2008 | Zdeblick et al. |
| 2009/0069867 A1 | 3/2009 | KenKnight et al. |
| 2009/0216132 A1 | 8/2009 | Orbach |
| 2009/0270747 A1 | 10/2009 | Van Dam et al. |
| 2009/0292194 A1 | 11/2009 | Libbus et al. |
| 2010/0022897 A1 | 1/2010 | Parker et al. |
| 2010/0081913 A1 | 4/2010 | Cross et al. |
| 2010/0185063 A1 | 7/2010 | Bardy |
| 2010/0191154 A1 | 7/2010 | Berger et al. |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089417 A1 | 4/2012 | Bardy et al. |

(56) References Cited

U.S. PATENT DOCUMENTS

2012/0101396 A1 4/2012 Solosko et al.
2013/0123651 A1 5/2013 Bardy
2013/0158361 A1 6/2013 Bardy

FOREIGN PATENT DOCUMENTS

| WO | WO2006/014806 | 2/2006 |
|---|---|---|
| WO | 2007092543 | 8/2007 |
| WO | WO2008/010216 | 1/2008 |
| WO | WO2009/112976 A1 | 9/2009 |
| WO | WO2009/112978 A1 | 9/2009 |
| WO | WO2009/112979 A1 | 9/2009 |
| WO | WO2010/066507 | 6/2010 |

OTHER PUBLICATIONS

Sittig et al., "A Computer-Based Outpatient Clinical Referral System," *International Journal of Medical Informatics*, Shannon, IR, vol. 55, No. 2, Aug. 1, 1999, pp. 149-158, XO004262434, ISSN: 1386-5056(99)00027-1.

Epstein, Andrew E. et al.; ACC/AHA/HRS 2008 Guidelines for Device-Based Therapy of Cardiac Rhythm Abnormalities. J. Am. Coll. Cardiol. 2008; 51; e1-e62, 66 Pgs.

Kligfield, Paul et al., Recommendations for the Standardization and Interpretation of the Electrocardiogram: Part I. J.Am. Coll. Cardiol; 2007; 49; 1109-27, 75 Pgs.

Lieberman, Jonathan, "How Telemedicine Is Aiding Prompt ECG Diagnosis In Primary Care," *British Journal of Community Nursing*, vol. 13, No. 3, Mar. 1, 2008, pp. 123-126, XP009155082, ISSN: 1462-4753.

EPO Extended Search Report for Application No. 11184156.5-2319/2438848 Dated Apr. 27, 2012, 10 Pgs.

EPO Extended Search Report for Application No. 11184382.7-2201 Dated Jan. 23, 2012, 11 Pgs.

EPO Extended Search Report for Application No. 11184379.3-1225 Dated Jan. 26, 2012, 6 Pgs.

EPO Extended Search Report for Application No. 11184344.7-1265/2438852 Dated Jun. 6, 2012, 6 Pgs.

EPO Extended Search Report for Application No. 11184341.3-1265/2438851 Dated Jun. 8, 2012, 6 Pgs.

EPO Extended Search Report for Application No. 11184353.8-1265/2438854 Dated Nov. 7, 2012, 10 Pgs.

EPO Extended Search Report for Application No. 11184347.0-1265/2438853 Dated Nov. 7, 2012, 11 Pgs.

Chen et al., "Monitoring Body Temperature Of Newborn Infants At Neonatal Intensive care Units Using Wearable Sensors," BodyNets 2010, Corfu Island, Greece. (Sep. 10-12, 2010).

Lauren Gravitz, "When Your Diet Needs A Band-Aid," Technology Review, MIT. (May 1, 2009).

15 Of The Hottest Wearable Gadgets—http://thehottestgadgets.com/2008/09/the-15-hottest-wearable-gadgets-001253.

US 6,527,714, 03/2003, Bardy (withdrawn)

| Bit | 11 | 10 | 9 | 8 | 7 | 6 | 5 | 4 | 3 | 2 | 1 | 0 |
|---|---|---|---|---|---|---|---|---|---|---|---|---|
| Content | \multicolumn{4}{c}{Header Indicator} | RESET | MARKER | \multicolumn{2}{c}{Reserved} | \multicolumn{4}{c}{Feedback} | though miniscule, the current flow can be measured to characterize the electrical activity of the heart using an electrocardiographic (ECG) monitor or similar device. Voltage differentials from pairings of the electrodes are filtered, amplified, and combined into P, QRS, and T complexes.
COMPUTER-IMPLEMENTED ELECTROCARDIOGRAPHIC DATA PROCESSOR WITH TIME STAMP CORRELATION

CROSS-REFERENCE TO RELATED APPLICATION

This non-provisional patent application is a continuation of U.S. patent application Ser. No. 12/901,460, filed Oct. 8, 2010, now patented as U.S. 8,239,012, the priority date of which is claimed and the disclosure of which is incorporated by reference.

FIELD

This application relates in general to electrocardiography and, in particular, to a computer-implemented electrocardiographic data processor with time stamp correlation.

BACKGROUND

The heart circulates blood throughout the body in a continual cycle of electrical stimulation of cardiac muscle cells. At rest, each muscle cell accumulates an electrical charge across its cell membrane that is then depolarized during each heartbeat. Initially, the cells of the sinoatrial node in the right atrium spontaneously depolarize and create a cardiac action potential of electrical impulses that rapidly propagates outward. The cardiac action potential stimulates muscle cells of the atrial myocardium to depolarize and contract in unison in systolic contraction, after which the cardiac action potential encounters the atrioventricular node located at the juncture of the atria and ventricles near the center of the heart. The atrioventricular node slightly delays cardiac action potential propagation to ensure complete drainage of blood from the atria after which the muscle cells of the ventricular myocardium are stimulated into systolic contraction and thereby complete the heart beat cycle.

The depolarization of the muscle cells of the atrial and ventricular myocardium act as sequential voltage sources, which generate a current flow across the thoracic region of the body and result in a characteristic signal on the body surface. In a typical ECG monitor, cardiac action potentials occur between 0.05 Hz to 150 Hz with a signal strength of around 3mVp-p (peak-to-peak). Although miniscule, the current flow can be measured to characterize the electrical activity of the heart using an electrocardiographic (ECG) monitor or similar device. Voltage differentials from pairings of the electrodes are filtered, amplified, and combined into P, QRS, and T complexes.

Conventionally, cardiac action potentials are detected through electrodes attached to the skin on the chest and limbs based on the American Heart Association's classic 12-lead placement model, such as described in P. Libby et al., "Braunwald's Heart Disease—A Textbook of Cardiovascular Medicine," Chs. 11 and 12 ($8^{th}$ ed. 2008), the disclosure of which is incorporated by reference. Both traditional in-clinic and ambulatory Holter-style ECG monitors follow the standard 12-lead model with variations on numbers and placement of leads. Generally, limb lead electrodes are placed on each arm and on the left leg, while precordial lead electrodes are placed on the left upper chest region over the heart. The limb leads can be re-positioned as necessary to compensate for variability in patient anatomy due to tissue and bone density and heart position.

Accurate ECG recording requires the absence of significant ambient noise. The 12-lead model attempts to maximize cardiac action potential signal strength. However, ECG monitors are still affected by environmental noise and feedback. The body acts as an antenna that is susceptible to electromagnetic (EMF) noise, which is often caused by power lines. Cardiac action potentials are inherently weak signals easily overwhelmed by such ambient interference. Skin-to-electrode impedance is around 51 kOhms. 50 Hz or 60 Hz power line EMF interference, depending on country, is filtered from the input signal using a filter, while baseline low-frequency wander is normally corrected by using a feedback system.

Conventional monitoring circuits combine physical shielding, analog filtering, and digital filtering to reduce noise. However, noise filtering methods can cut dynamic range, particularly low frequency sensitivity, to keep signals within a permissible dynamic range. As a consequence, ECG quality and clinical value can suffer when extremely low frequency content is lost. There are a variety of analog feedback circuits in conventional ECG monitors to drive a common mode voltage and keep the amplifiers from oversaturation. For instance, in a right leg drive (RLD) circuit, a network of resistors sense common mode voltage on a body, which is then inverted, amplified, and fed back into the body through a reference electrode. Consequently, the body becomes a summing junction in a feedback loop. Negative feedback thereafter drives common mode voltage to a nominal value.

Although effective at countering respiration, wander and drift, such conventional analog RLD circuits increase circuit complexity and cost and destroy very low frequency content. Even though RLD circuits typically drive less than one microampere of current into the right leg, at a minimum, a resistor feedback network and an output op-amp that drives a reference electrode must be powered and placed in the circuit. The constant power draw to drive the circuit can tax power budget constraints, particularly where the circuit is in an ambulatory battery-powered ECG monitor.

For instance, U.S. Pat. No. 5,392,784, issued Feb. 28, 1995 to Gudaitis, discloses a virtual right leg drive circuit for common mode voltage reduction. A circuit senses common mode voltage received by inputs from a signal amplifier and generates a compensation voltage, representative of the common mode voltage. A capacitance to chassis ground receives a voltage representative of the compensation voltage. The circuit and the capacitance cause the amplifier power supply voltages to track the common mode voltage. The capacitance permits the feedback loop gain to be increased to reduce common mode voltage errors, but at the cost of increased circuit complexity.

U.S. Patent application, Publication No. 2007/0255153, filed Nov. 1, 2007, to Kumar et al., now patented as U.S. Pat. No. 8,160,682; U.S. Patent application, Publication No. 2007/0225611, filed Feb. 6, 2007, to Kumar et al., now patented as U.S. Pat. No. 8,244,335; and U.S. Patent application, Publication No. 2007/0249946, filed Feb. 6, 2007, to Kumar et al., now patented as U.S. Pat. No. 8,150,502, disclose a non-invasive cardiac monitor and methods of using continuously recorded cardiac data. A heart monitor suitable for use in primary care includes a self-contained and sealed housing. Continuously recorded cardiac monitoring is provided through a sequence of simple detect-store-offload operations. An action sequencer state machine directs the flow of information to either memory or to a switched I/O unit without feedback control. In one embodiment, a 24-bit analog-to-digital converter converts continuously detected ECG information into uncompressed 8-bit data. Amplification circuitry is not required, as amplification and scaling are replaced by selecting an 8-bit data resolution out of a possible 24-bit range. Additionally, the 24-bit to 8-bit selector serves as a scaler to keep signal excursions within the numeric range of the analog-to-digital converter and to provide image scaling to the end user. The stored ECG data can be retrieved and analyzed offline to identify ECG events.

U.S. Patent application, Publication No. 2008/0284599, filed Apr. 28, 2006, to Zdeblick et al., pending, and U.S. Patent application, Publication No. 2008/0306359, filed Dec. 11, 2008, to Zdeblick et al., pending, disclose a pharmainformatics system for detecting the actual physical delivery of a pharmaceutical agent into a body. An integrated circuit is surrounded by pharmacologically active or inert materials to form a pill, which dissolve in the stomach through a combination of mechanical action and stomach fluids. As the pill dissolves, areas of the integrated circuit become exposed and power is supplied to the circuit, which begins to operate and transmit an information signal. A signal detection receiver can be positioned as an external device worn outside the body with one or more electrodes attached to the skin at different locations. The receiver can include the capability to provide both pharmaceutical ingestion reporting and psychological sensing in a form that can be transmitted to a remote location, such as a clinician or central monitoring agency.

Therefore, a need remains for an approach to efficiently negate the affects of environmental interference, while preserving dynamic signal range in an ECG monitor and simultaneously reducing the complexity of ECG circuitry, especially for designs intended for low-cost and disposable ECG monitoring technologies.

SUMMARY

A monitoring circuit for ECG recording operates under microprogrammed control on a single channel of analog input signals. The signals originate as cardiac action potentials sensed from the skin's surface by a single sensing electrode pair, although multiple sensing electrode pairs could be employed with modifications to the monitoring circuit to factor in multiple input signal channels. The monitoring circuit provides digitally-controlled feedback in lieu of employing a conventional right leg drive or similar feedback circuit. The analog input signals are converted into digitized form and encoded for efficient compressed data storage in non-volatile memory. Feedback markers are stored with the digitized data. Following monitoring, the discrete digital values can be retrieved from the non-volatile memory and the original analog signal can be reproduced. The digitization and compression of the original analog signal requires less memory to store long term ECG data while providing improved signal reproduction accuracy. The accuracy of the reproduced analog signal can be improved by correcting the decoded data for power supply depletion. As well, the resolution of the signal can be increased by removing any feedback that was introduced by the microcontroller during monitoring.

One embodiment provides a computer-implemented electrocardiographic data processor with time stamp correlation. A download station includes a data interface that is configured to physically interface to an electrocardiographic monitoring circuit. The monitoring circuit includes a persistent memory and an onboard power supply that powers an encoder configured to determine a differential voltage between a current discrete digital voltage value and a prior discrete digital voltage value. The differential voltage is stored into the persistent memory in a digitized data stream representative of analog cardiac action potential signals. The download station further includes a data retrieval module that is configured to retrieve digitally-encoded voltage values and time stamps recorded by the monitoring circuit from the persistent memory of the monitoring circuit via the data interface. A post-processing application is configured to execute on a computer that is interfaced with the download station. An onboard digital data store includes a set of enumerated output voltages and enumerated ranges of voltage differences that each correspond to lower and upper bounds of voltage. A comparator is configured to compare each retrieved voltage value to the lower and upper bounds of voltage and to identify the enumerated range within which each retrieved voltage value falls. A decoder is configured to select the output voltages corresponding to the identified enumerated ranges as a reproduction of the analog cardiac action potential signals. A display is configured to depict the reproduced analog cardiac action potential signals and to correlate the time stamps to temporal points within the reproduced analog cardiac action potential signals.

A further embodiment provides a computer-implemented electrocardiographic data processor with feedback cancellation. A download station includes a data interface configured to physically interface to an electrocardiographic monitoring circuit. The monitoring circuit includes a persistent memory and an onboard power supply that powers an encoder configured to determine a differential voltage between a current discrete digital voltage value and a prior discrete digital voltage value. The differential voltage is stored into the persistent memory in a digitized data stream representative of analog cardiac action potential signals. The download station further includes data retrieval module configured to retrieve digitally-encoded voltage values and feedback markers recorded by the monitoring circuit from the persistent memory of the monitoring circuit via the data interface. A post-processing application is configured to execute on a computer that is interfaced with the download station. An onboard digital data store includes a set of enumerated output voltages and enumerated ranges of voltage differences that each correspond to lower and upper bounds of voltage. A bias settings module is configured to determine, based on the retrieved feedback markers, bias control settings used during recording of the analog cardiac action potential signals. A comparator is configured to compare each normalized voltage value to the lower and upper bounds of voltage and to identify the enumerated range within which each normalized voltage value falls. A decoder is configured to select the output voltages corresponding to the identified enumerated ranges as a reproduction of the analog cardiac action potential signals. A feedback cancellation module is configured to determine a contribution from feedback introduced by application of the bias control settings and to subtract the feedback contribution from the reproduced analog cardiac action potential signals.

A still further embodiment provides computer-implemented electrocardiographic data processor with voltage depletion compensation. A download station includes a data interface configured to physically interface to an electrocardiographic monitoring circuit. The monitoring circuit includes a persistent memory and an onboard power supply that powers an encoder configured to determine a differential voltage between a current discrete digital voltage value and a prior discrete digital voltage value. The differential voltage is stored into the persistent memory in a digitized data stream representative of analog cardiac action potential signals. The download station further includes a data retrieval module configured to retrieve digitally-encoded voltage values recorded by the monitoring circuit over a fixed monitoring period from the persistent memory of the monitoring circuit via the data interface. A post-processing application is configured to execute on a computer that is interfaced with the download station. An onboard digital data store includes a set of enumerated output voltages and enumerated ranges of voltage differences that each correspond to lower and upper bounds of voltage. A reference voltage module is configured to determine an adjusted voltage of the power supply for each retrieved voltage value as a function of the number of voltage values recorded prior to the retrieved voltage value. A voltage normalizer is configured to normalize each retrieved voltage value against the power supply's adjusted voltage. A comparator is configured to compare each normalized voltage value to the lower and upper bounds of voltage and to identify the enumerated range within which each normalized voltage value falls. A decoder is configured to select the output voltages corresponding to the identified enumerated ranges as a reproduction of the analog cardiac action potential signals.

A yet further embodiment provides a microcontrolled electrocardiographic monitoring system. A microcontrolled electrocardiographic monitoring circuit includes a microcontroller circuit, which includes an input codec. The microcontroller circuit further includes an analog-to-digital converter connected to a filtered amplified analog input signal path that is configured to convert the input signal into a data stream of discrete digital values. The microcontroller circuit further includes an encoder configured to determine a differential voltage between a current digital value and a prior digital value in the data stream. The microcontroller circuit further includes a feedback generator configured to identify a pairing of drive resistor settings matched to each digital value in the data stream and to output the drive resistor settings as a digital feedback signal. The microcontroller circuit finally includes an drive resistor adjuster configured to adjust each drive resistor in an output signal path according to the digital feedback signal. The monitoring circuit further includes persistent memory connected to the microcontroller circuit configured to store the differential voltages for each of the digital values. A download station includes a data interface configured to physically interface to the monitoring circuit and a data retrieval module configured to retrieve digitally-encoded data values representative of analog cardiac action potential signals from the persistent memory of the monitoring circuit via the data interface. A post-processing application is configured to execute on a computer that is interfaced with the download station. An onboard digital data store includes a set of enumerated output voltages and enumerated ranges of voltage differences that each correspond to lower and upper bounds of voltage. A comparator is configured to compare each retrieved data value to the lower and upper bounds of voltage and to identify the enumerated range within which each retrieved data value falls. A decoder is configured to select the output voltages corresponding to the identified enumerated ranges as a reproduction of the input signal.

The microcontrolled ECG monitoring circuit offers a lower power design, has a lower component and power cost, and provides flexible control over input signal processing, as well as providing better post-processing options with extended dynamic range. The circuit is particularly suited to ambulatory ECG monitoring from a midline sternum-centered position, which provides a superior body position for home application and for patient comfort when used for long-term monitoring, despite the need for stronger cardiac action potential signal amplification to compensate for a short signal vector characteristic of this sternal location. In contrast, conventional ECG monitoring circuits would saturate at comparably high signal amplification levels and rely on modifying lead placement to compensate for patient physical variability.

Further, the microcontrolled ECG monitoring circuit enables an ambulatory ECG monitor to be built at low cost, size and weight. For instance, a disposable ECG monitor in the form of an adhesive patch can be constructed with a weight of less than one ounce and inter-electrode spacing of less than 6 cm, which presents three advantages. First, costs for shipping the monitors to clinics, hospitals, pharmacies, and other locations are reduced, especially when large quantities must be mailed around the world. Second, small size and weight ambulatory ECG monitors can be easily carried in the pockets of health care providers and therefore applied upon demand without the need to either retrieve the monitors from a special location or to send the patient to a separate laboratory. Third, small, lightweight ambulatory ECG monitors reduce shear forces on the skin, which further ensures good signal acquisition and long-term ECG recording by facilitating adherence to the skin and comfort for the patient.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Figure 1:
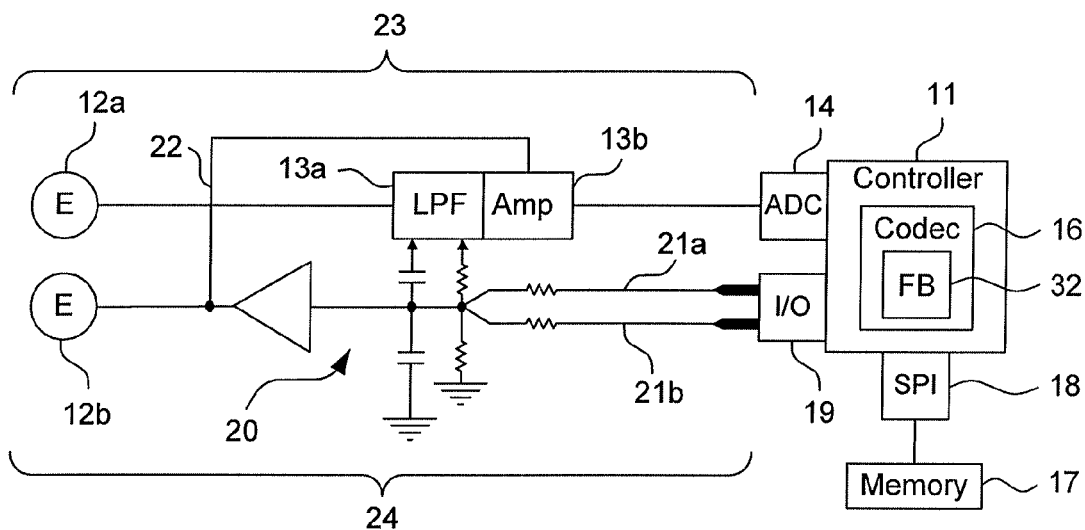
FIG. 1 is a schematic diagram showing a microcontrolled electrocardiographic monitoring circuit with differential voltage encoding in accordance with one embodiment.

Low pass and high pass filters attenuate input signals to remove noise and other undesirable components of an electrocardiographic signal. Physical shielding increases weight and affects the selection of housing materials. Further, traditional feedback circuits, such as right leg drive (RLD) circuits, introduce added circuit complexity, raise component cost, and require increased power to drive inverted common mode voltage into the body as negative feedback. Conventional approaches are unsatisfactory when used in an ECG monitor for extended operation, particularly in ambulatory ECG monitoring that can potentially capture and record a large body of physiological data, while being reliant on a self-contained and finite power source.

Moreover, conventional forms of ECG monitoring, including ambulatory ECG monitoring, rely on the standard 12-lead placement model, which places the precordial lead electrodes over the left upper chest in close proximity to the heart and at a location of strongest ventricular cardiac action potential signal strength. In turn, the monitoring circuitry relies on the superior signal strength from over-the-heart electrode placement and the relatively long signal vector length that is afforded by lead placement over a wider physical expanse of the body. For instance, signal amplification assumes a signal strength of around 3 mVp-p (peak-to-peak).

The 12-lead placement model, however, is poorly suited to long term ambulatory monitoring. In addition, recording of the atrial cardiac action potential (or P-Wave) can be inadequate thereby interfering with arrhythmia diagnosis. Moreover, in-clinic ECG monitoring assumes the patient will remain relatively stationary and limb leads can be repositioned as necessary to compensate for variability in patient anatomy. In contrast, during ambulatory monitoring, a patient's body is in continual motion, even during sleep, albeit to a lesser degree. Electrodes are apt to detach and the quality of signal acquisition depends on the degree to which each electrode maintains its original position.

Ambulatory ECG monitoring can be improved by locating the lead electrodes to body positions better adapted to minimize artifacts due to body movement. Although rarely used, no position is better suited for ease of application and P-wave signal acquisition during ambulatory ECG monitoring than the patient's chest at midline, covering the center third of the sternum and centered mid-sternum between the manubrium and the xiphoid process. This location provides a superior location for long term ambulatory monitoring, such as described in commonly-assigned U.S. Patent application, Publication No. 2012/0089001, filed Oct. 8, 2010, to Bishay et al, the disclosure of which is incorporated by reference. A pair of electrodes, spaced less than 6 cm apart, are placed midline in a narrow patch electrode designed to conform to the sternal surface, which is non-planar, even in men. In one embodiment, the electrodes have an approximately 2.5 cm spacing. The midline sternum-centered monitoring site enables both good amplitude P-wave and QRS-wave acquisition. However, the electrode placement results in a short signal vector that diminishes signal strength to about 25% of the signal amplitude obtainable from more widely spaced electrodes as used in traditional ECG monitoring technologies.

Digitally-controlled ECG monitoring circuits provide the ability to handle the wide dynamic range occasioned by the short signal vector and low signal strength afforded by a midline sternum-centered ambulatory monitoring location. FIG. 1 is a schematic diagram showing a microcontrolled ECG monitoring circuit 10 with differential voltage encoding in accordance with one embodiment. The monitoring circuit 10 can be used in all forms of ECG monitoring, including traditional in-clinic ECG monitoring, but is particularly suited to self-powered ambulatory ECG monitoring for use over an extended period of one to 30 days or longer. For clarity, only the principal components of the monitoring circuit 10 proper will be discussed. Ancillary components, such as power supply, external device interface, and support circuitry, will be skipped.

The components of the monitoring circuit 10 are specifically selected to reduce overall cost. In one embodiment, the monitoring circuit 10 operates on a single channel of analog input signals. The signals originate as cardiac action potentials sensed on the skin's surface by two electrodes 12a, 12b, although multiple sensing electrodes could be employed with modifications to the monitoring circuit to factor in multiple input signal channels. The analog components define two low capacitance signal paths 23, 24 for respectively providing the analog input signal and driving a microcontroller-determined output signal into the body. The input signal path 23 includes an input electrode 12a connected in-line to a low pass filter (LPF) 13a and an amplifier 13b. The input electrode 12a has a conductive surface, such as silver-silver chloride, for sensing cardiac action potentials on the skin's surface. The output signal path 24 includes an output electrode 12b connected inline to a buffer circuit 20 and a pair of drive resistors 21a, 21b that are connected in parallel. The output electrode 12b similarly has a conductive surface, such as silver-silver chloride, and drives a feedback signal to cancel out very low frequency bias, which could be caused by ECG electrode mismatch or other causes.

The digital components include a microcontroller 11 and persistent non-volatile memory 17, such as electrically-erasable programmable read-only memory (EEPROM) or "flash" memory. The microcontroller 11 includes components conventionally found in micro control processors, including accumulators, comparators, and related logic components. In one embodiment, the microcontroller is an R8C/M12 microcontroller, manufactured by Renesas Electronics Corporation, Tokyo, Japan. The monitoring circuit 10 operates under the control of the microcontroller 11 that executes an instruction set (not shown) persistently stored as firmware in the non-volatile memory 17. Alternatively, the instruction set can be stored in a programmable logic array (PLA), volatile random access memory (RAM), or other forms of microcontroller-readable storage structure. The instruction set defines the type of feedback and form of encoding employed by the microcontroller 11. The instruction set can be changed to meet different accuracy requirements. Accuracy generally entails a tradeoff between input frequency bandwidth and sampling. In turn, changes to those factors affect the encoding or compression ratio, CPU utilization, and power budget.

The microcontroller 11 is interfaced to the input signal path 23 through an on board analog-to-digital controller 14 (ADC) connected to the output of the low pass filter 13a and the amplifier 13b, which receive a reference signal 22 from the output of buffer circuit 20. The analog signals are of low amplitude. Due to the sternum-centered location of the input electrode 12b, the amplifier 13b must boost an analog input signal of around 0.5-3 mVp-p with a signal-to-noise ratio (SNR) of about 80 dB. The exceptional SNR found in the sternal location improves waveform quality and partially compensates for the short signal vector resulting from close electrode placement. In contrast, the noise floor encountered by a conventional ECG monitoring circuit is typically much higher and comparable amplification would result in a poor signal with low amplitude, rather than a usable data signal.

A conventional RLD circuit applies negative feedback into the patient's body to drive common mode voltage to a nominal value, but at the expense of additional circuit complexity, cost, and weight. In contrast, the monitoring circuit 10 uses the reference signal 22 to inject a feedback signal into both the ADC 14, the amplifier and the patient's body. Thus, circuit noise is injected into the input signals, rather than being filtered. The monitoring circuit 10 is thereby able to operate without physical shielding, with minimal analog filtering, no digital filtering, and with minimal power filtering components, when used in an ambulatory ECG monitor. Physical noise shielding is eliminated through unique printed circuit board design and layout, as well as careful selection of electronic components that naturally dampen unwanted signals.

The ADC 14 converts the analog input signal into a discrete digital value. In one embodiment, the discrete digital values are generated by the ADC 14 with a 12-bit resolution at a 176 Hz sampling rate, although other sample sizes and sampling rates are often utilized. The microcontroller 11 is interfaced to the output signal path 24 through an input/output module 19 (I/O). The I/O module 19 converts a digital feedback signal, as further described below with reference to FIG. 2. The microcontroller 11 is interfaced to the non-volatile memory 17 through serial peripheral interface bus module (SPI) 18 that synchronously reads and writes data frames of digital values to and from the non-volatile memory 17. The microcontroller 11 could also be interfaced to other analog and digital components and to monitor other physiological signals.

Figure 2:
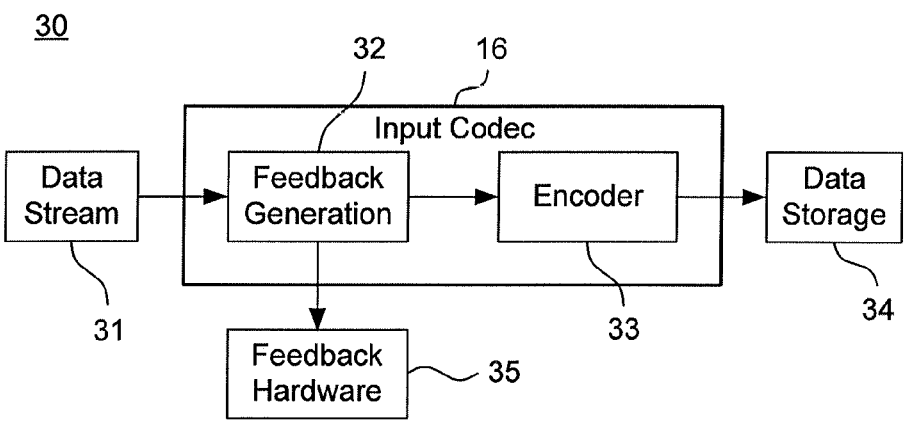
FIG. 2 is a functional block diagram showing an input codec for the monitoring circuit of FIG. 1.

The firmware-stored instruction set functionally defines an input coder/decoder (codec) 16 that manages onboard processing of the digitally-converted analog input signal for sensed cardiac action potentials. FIG. 2 is a functional block diagram showing an input codec 16 for the monitoring circuit 10 of FIG. 1. In one embodiment, the input codec 16 is optimized to ignore clinically insignificant variations in the data to achieve improved compression ratios through data encoding. The digitization and compression of the original analog signal requires less memory to store long term ECG data while providing improved signal reproduction accuracy. Alternatively, clinically insignificant variations could be processed, but at the cost of increased processing complexity, lowered storage capacity, and faster power depletion.

The input codec 16 functionally defines a feedback generation module 32 and encoder 33. The feedback generation module 32 receives a data stream 31 of discrete digital values from the ADC 14. In one embodiment, the feedback generation module 32 selectively samples every fourth value, although other feedback sampling frequencies could be utilized, including sampling of every digital value received.

When the input signal approaches a bias threshold of ±10% of the maximum level of the system, the mode number is adjusted. For example, if the input signal reaches +10% of the maximum value, the mode number is incremented by one and the feedback is adjusted accordingly. Feedback levels are defined for an enumerated set of feedback modes, as shown, by way of example, in Table 1. Each feedback mode (Column 1) specifies bias controls for a pair of drive resistors 21a, 21b and corresponds to a range of lower and upper bound threshold tolerances, here, shown as percentages of maximum amplitude saturation level for the amplifier 13b (Column 3). The bias controls determine the value of the feedback signal (Column 2) that is used to adjust the pair of drive resistors 21a, 21b during monitoring.

TABLE 1

| Mode | Values of Drive Resistors | Mode Number |
|---|---|---|
| Fast High | Both Resistors Drive High | 2 |
| High | One Resistor Drives High | 1 |
| Off | One Resistor Drives Low, One Resistor Drives High | 0 |
| Low | One Resistor Drives Low | −1 |
| Fast Low | Both Resistors Drive Low | −2 |

Other ranges of threshold tolerances could be utilized, such as subthresholds representing values for the input digital value that are less than the bias saturation threshold. Furthermore, instead of constant outputs to the drive resistors, a pulse width modulated signal could be provided to increase dynamic range.

The input value is compared to each of the ranges of bias saturation thresholds by the feedback generation module 32. Feedback is activated when the input signal gets too close to the saturation point of the input amplifier 13b, such as described in commonly-assigned U.S. Patent application, Publication No. 2012/0089036, filed Oct. 8, 2010, to Felix et al., the disclosure of which is incorporated by reference. For instance, an input digital value reflecting a signal strength of up to 10% of the maximum amplitude saturation level results in a feedback signal that increases the amount of positive feedback that changes the drive settings of the drive resistor 21a, 21b. The range of threshold closest to, but not exceeding, the input value is generally selected, although other selection criteria could alternatively be used. The feedback signal is expressed as a pair of settings for the drive resistors 21a, 21b, which are output through feedback hardware 35 that includes the input/output module 19 and circuitry to convert the two drive resistor settings into analog signals. The outputs of the drive resistors 21a, 21b feed into the buffer circuit 20 and are driven into the body through the output electrode 12b as feedback.

To enable resolution extension during post-processing, the feedback generation module 32 also injects a feedback marker in sequence into the data stream 31 to indicate the change in feedback mode. In one embodiment, the feedback marker is included in a three-nibble header, further described below with reference to FIG. 3, although other types of data markers could be utilized. In a further embodiment, the feedback generation module 32 employs hysteresis to help prevent too frequent changes in feedback mode.

The encoder 33 employs discrete variable slope encoding to store the digitally-converted analog input signals for sensed cardiac action potentials in an encoded or compressed form. The encoder 33 receives the data stream 31 from the feedback generation module 32. The encoder 33 then determines the difference in voltage between the current digital value and the prior value output by the input codec 16 to data storage 34 that includes the non-volatile storage 17.

Encoding the voltage differentials between successive digitized input signals provides more efficient data storage than storing each discrete voltage, while still retaining the ability to reproduce the original analog input signal during post-monitoring data analysis. A file system is not required and variable slope encoding provides a 3:1 compression ratio for 12-bit input, in contrast to the more typical 1.5:1 compression ratio used in conventional ambulatory ECG monitors utilizing traditional run-length-based encoding. Voltage differential encoding is also memory and process efficient. In one embodiment, the voltage differences are stored as nibbles that represent four-bit signed integers, where a most-significant-bit set to high indicates a negative value. To retain whole byte alignment in memory, the nibbles are first accumulated into single-byte or multi-byte values before being written out to the data storage 34, although other sizes of data storage elements, such as half-word, word, and block sizes, and deferred or immediate data write-out schemes could be utilized.

The differences in voltages may be positive or negative. Each voltage difference is encoded by use of an encoding table, as shown, by way of example, in Table 2. The voltage difference must fall within an enumerated range of input values (Column 1) and is encoded (Column 3). The output values (Column 2) corresponding to each enumerated range are used to reproduce the original input signal. If the input and output values cannot be matched, the difference between the values is recorded and is used to calculate the next output value.

TABLE 2

| Input Value | Output Value | Encoded Value |
|---|---|---|
| >32 | 32 | 7 |
| 31 to 24 | 24 | 6 |
| 23 to 16 | 16 | 5 |
| 15 to 8 | 8 | 4 |
| 7 to 4 | 4 | 3 |
| 2 to 3 | 2 | 2 |
| 1 | 1 | 1 |
| 0 | 0 | 0 |

TABLE 2-continued

| Input Value | Output Value | Encoded Value |
| --- | --- | --- |
| −1 | −1 | −1 |
| −2 to −3 | −2 | −2 |
| −7 to −4 | −4 | −3 |
| −15 to −8 | −8 | −4 |
| −23 to −16 | −16 | −5 |
| −31 to −24 | −24 | −6 |
| <−32 | −32 | −7 |
| Header | Header | −0 |

The enumerated ranges for the input values in the encoding table can also be changed to support increased accuracy at the cost of decreased high frequency response performance, or vice versa.

Figures 3, 4:
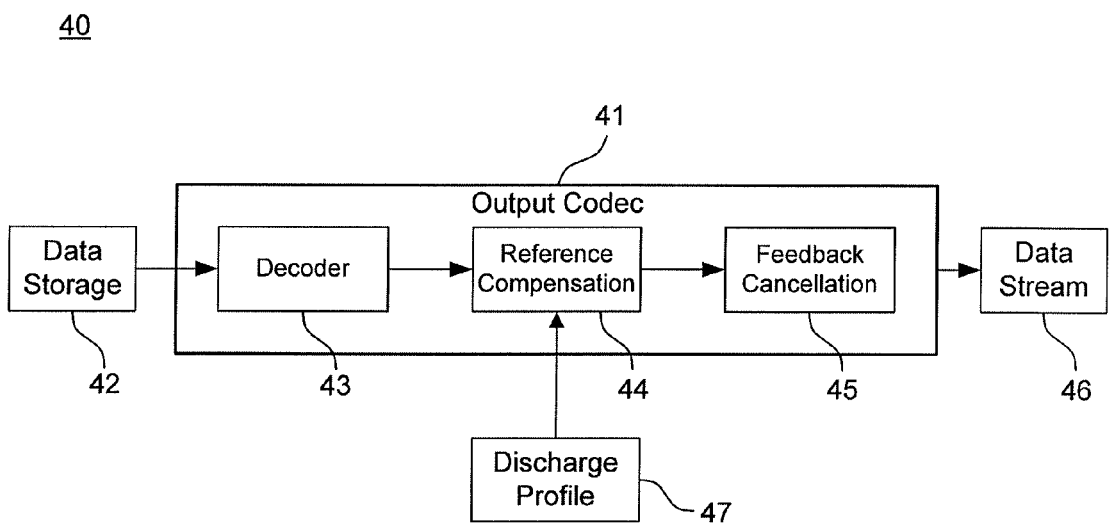
FIG. 3 is a block diagram showing, by way of example, a header schema used by the monitoring circuit of FIG. 1.
FIG. 4 is a functional block diagram showing an output codec for the monitoring circuit of FIG. 1.

Voltage differences between sensed activation potential voltages are recorded as discrete digital values in a continuous data stream stored in non-volatile memory. Additionally, events are recorded in headers inserted into the data stream for use during post-processing. FIG. 3 is a block diagram showing, by way of example, a header schema used by the monitoring circuit 10 of FIG. 1. In one embodiment, each header is three nibbles long, with the first nibble containing a header indicator. Headers are marked with negative zero values, although other marker values could be used. The body of the header indicates three types of events: resets, button presses, and changes in feedback, described supra. A reset can occur when the monitoring circuit 11 encounters a predefined condition, generally representing an error or alarm that requires the circuit to be reset. A reset is marked in the data stream by setting the output value to the value of the nibble that precedes the header. A button press records the physical pressing of a switch or button on the ECG monitor itself, where supported by the hardware. Finally, feedback marker is stored as the last nibble in the header. Other header schemas and content could be utilized.

Data decoding is performed offline, which physically interfaces to the monitoring circuit 10 and retrieves the recorded data stream from the non-volatile memory 17 through a download station. The retrieved data stream is then processed by a computer workstation that executes a post-processing application that implements an output codec to reproduce the original cardiac action potential signal. FIG. 4 is a functional block diagram showing an output codec 41 for the monitoring circuit 10 of FIG. 1. The computer workstation can either be a purpose-built device or personal computer executing application programs. The output codec 41 is implemented in firmware or software as a set of instructions for execution by the computer workstation.

The output codec 41 functionally defines a decoder 43, reference compensation module 44, and feedback cancellation module 45. The decoder 43 retrieves stored voltage differences from data storage 42, which generally will be the non-volatile memory 17 of the monitoring circuit 11 if the data has not yet been physically retrieved from the ECG monitor. In one embodiment, the voltage differences of the cardiac action potentials are encoded as nibbles that represent four-bit signed integers with headers encoded using three contiguous nibbles.

The decoder 43 processes the data retrieved from the data storage 42 on a nibble-by-nibble basis. Each nibble represents a voltage difference over the last observed voltage. Each retrieved data value is decoded into its corresponding output value, as shown, by way of example, in Table 2. In one embodiment, the decoded values are 12-bit digital values, which reflects the original 12-bit resolution used during sampling, although other sizes could be utilized. The decoded values can be extended to much higher resolutions through feedback cancellation, as further described infra.

The first nibble of every header contains a negative zero nibble. Thus, upon encountering a negative zero nibble, the next byte of data is processed by the decoder 43 to identify the event represented, that is, a reset, a button press, feedback, or a combination thereof. Thereafter, the event is processed by the download station, or offline, as appropriate. For instance, a button press event may cause the download station to place a visual indication and time stamp in the QRS complex that is ultimately reproduced from the recorded set of voltage differences. In turn, the time stamp can be correlated with subjective impressions recorded by the patient in a personal diary during the period of monitoring, such as described in commonly-assigned U.S. Patent application, Publication No. 2012/0088998, filed Oct. 8, 2010, to Bardy et al., pending, the disclosure of which is incorporated by reference. Similarly, a reset event may signal a programmatic error that requires debugging, a hardware concern, including component fault, software failure, or other considerations underlying monitoring circuit reset.

The sensitivity of the monitoring circuit 10 increases over time as its finite power supply is depleted. Thus, following decoding, the reference compensation module 44 receives the retrieved data, which is then normalized to counteract the affect of power supply depletion over the monitoring period. The decoded values are scaled based on the discharge profile 47 of the ECG monitor's power supply, typically a battery or similar finite power cell. The analog components of the monitoring circuit 10 are referenced to the power supply. During runtime, battery voltage quickly decreases and then stays constant for most of the discharge profile, then quickly ramps down again. To maintain accuracy, the voltages represented by each of the discrete digital values decoded by the decoder 43 must be adjusted to account for battery discharge. Writing data to non-volatile memory requires the most power. The number of write operations into the non-volatile memory can be determined based on the total number of samples. The amount of voltage correction required can be determined based on the placement of a particular sample within the ordering of the total body of samples recorded. For instance, a sample recorded at the beginning of a monitoring period will be most affected by battery depletion than a sample recorded much later in the period.

Corrected voltage V for each discrete decoded data value can be determined based on the equation:

$$V = D \cdot \frac{B[S]}{2^b} \quad (1)$$

where D is the decoded value, B is the battery voltage as a function of the number of the sample S, and b is the number of bits in the input stream. The corrected voltage will typically fall in the range of 0-3.2 VDC, while the battery voltage varies between 2.7-3.2 VDC. The number of samples will depend on the capacity of the non-volatile memory. For example, a 32 MB memory can store between 0-2*$2^{25}$ samples. Other discharge profile adjustments could be utilized.

During ECG monitoring, feedback is introduced to avoid saturating the input amplifier 13b. A feedback marker is added to the data stream to indicate the change in feedback mode. During post-processing, the feedback can be removed to extend the effective dynamic range of the monitoring data. The data resolution, as expressed by number of bits n, can be determined based on the equation:

$$n = \frac{\ln(a)}{\ln(2)} + b \quad (2)$$

where a is an amplification factor and b is the number of bits in the decoded input stream. The amplification factor can range up to around 750, depending upon the circuit layout and particularly on the op-amp used. In one embodiment, the effective number of bits doubles the resolution to 20-bits. Other data resolution values could be achieved.

The affects of feedback on the data stream are removed by subtracting the feedback's contribution $E_{RLD}$, which can be determined based on the equation:

$$E_{RLD} = \frac{C}{2}\left(V_{O_{RLD}} e^{\frac{-t}{R_{RLD} \cdot C}}\right)^2 \quad (3)$$

where C is the parasitic capacitance of the patient, $V_{O_{RLD}}$ is the last voltage output on the feedback circuit, $R_{RLD}$ is the output resistance value of the feedback circuit, and T is the time between samples. The energy contribution of the RLD can be converted into voltage, which can be determined based on the equation:

$$V = \sqrt{\frac{C}{2E_{RLD}}} \quad (4)$$

where V is the voltage contribution of the feedback circuit, C is the self capacitance of the patient and $E_{RLD}$ is the energy contribution of the right leg drive. Other feedback cancellation methodologies could also be employed.

While the invention has been particularly shown and described as referenced to the embodiments thereof, those skilled in the art will understand that the foregoing and other changes in form and detail may be made therein without departing from the spirit and scope of the invention.

What is claimed is:

1. A computer-implemented electrocardiographic data processor with time stamp correlation, comprising:
    a download station, comprising:
        a data interface configured to physically interface to an electrocardiographic monitoring circuit, the monitoring circuit comprises a persistent memory, an onboard power supply, and an encoder powered by the onboard power supply and configured to determine a differential voltage between a current discrete digital voltage value and a prior discrete digital voltage value, the differential voltage is stored into the persistent memory in a digitized data stream format representative of analog cardiac action potential signals; and
        a data retrieval module configured to retrieve digitally-encoded voltage values and time stamps recorded by the monitoring circuit from the persistent memory of the monitoring circuit via the data interface;
    a post-processing application configured to execute on a computer that is interfaced with the download station, comprising:
        an onboard digital data store comprising a set of enumerated output voltages and enumerated ranges of voltage differences that each correspond to lower and upper bounds of voltage;
        a comparator configured to compare each retrieved voltage value to the lower and upper bounds of voltage and to identify the enumerated range within which each retrieved voltage value falls; and
        a decoder configured to select the output voltages corresponding to the identified enumerated ranges as a reproduction of the analog cardiac action potential signals; and
    a display configured to depict the reproduced analog cardiac action potential signals and to correlate the time stamps to temporal points within the reproduced analog cardiac action potential signals.

2. A data processor according to claim 1, further comprising:
    the set of enumerated output voltages further comprising mirrored pairs of positive and negative output voltages that exponentially increase with a number of bits used to encode each discrete digital voltage value.

3. A data processor according to claim 1, further comprising:
    a signal modeler configured to interpret a discrete variable slope encoding implicit in the digitally-encoded voltage values as recorded in the persistent memory of the monitoring circuit into the reproduced analog cardiac action potential signals based on the output voltages.

* * * * *